(12) United States Patent
McNamara

(10) Patent No.: US 6,524,269 B2
(45) Date of Patent: Feb. 25, 2003

(54) LUBRICATED TAMPON

(76) Inventor: Sean P. McNamara, 7003 Kenneth Dr., Annandale, VA (US) 22003

( * ) Notice: Subject to any disclaimer, the term of this patent is extended or adjusted under 35 U.S.C. 154(b) by 0 days.

(21) Appl. No.: 09/848,365

(22) Filed: May 4, 2001

(65) Prior Publication Data

US 2002/0026140 A1 Feb. 28, 2002

Related U.S. Application Data

(60) Provisional application No. 60/222,606, filed on Aug. 2, 2000.

(51) Int. Cl.[7] .................................................. A61F 13/20
(52) U.S. Cl. ............................ 604/12; 604/14; 604/15; 604/904; 604/363
(58) Field of Search ........................... 604/11–18, 904, 604/385.18, 57–60, 363

(56) References Cited

U.S. PATENT DOCUMENTS

| | | |
|---|---|---|
| 2,734,505 A | 2/1956 | Parish |
| 3,139,886 A | 7/1964 | Tallman et al. |
| 3,335,726 A | 8/1967 | Maranto |
| 3,390,671 A | 7/1968 | Hildebrand |
| 3,428,044 A | 2/1969 | Whitehead et al. |
| 3,595,236 A | 7/1971 | Corrigan et al. |
| 3,724,465 A | 4/1973 | Duchane |
| 3,791,385 A | 2/1974 | Davis et al. |
| 4,312,348 A * | 1/1982 | Friese .......................... 604/363 |
| 4,421,504 A | 12/1983 | Kline |
| 4,428,747 A | 1/1984 | Friese et al. |
| 4,690,671 A | 9/1987 | Coleman et al. |

FOREIGN PATENT DOCUMENTS

| | | |
|---|---|---|
| DE | 2244586 | 9/1972 |
| JP | 4-322647 | 11/1992 |

* cited by examiner

*Primary Examiner*—Dennis Ruhl
*Assistant Examiner*—C. Lynne Anderson
(74) *Attorney, Agent, or Firm*—Richard C. Litman

(57) ABSTRACT

A lubricated tampon applicator having a sanitary wrapper. The applicator comprises a tubular body having a lubrication cell near its insertion end. The lubrication cell is scored to preferentially fail first at the interior cell membrane, and then the exterior cell membrane as the tampon is expelled from the applicator. The tampon has a lesser circumference about the leading portion than the trailing portion, thereof. In another embodiment the cell is a cage having a scored inner membrane and a leading surface of discrete petals. The cage is covered by an elastic membrane which is turned inward at the central axis and extends through an opening formed by the petals, flares radially outward, and seals against the inner membrane. The sanitary wrapper contains a portion for maintaining the applicator tip coated with lubricant. An adhesive bonds the wrapper to the applicator, effectively containing the lubricant.

19 Claims, 12 Drawing Sheets

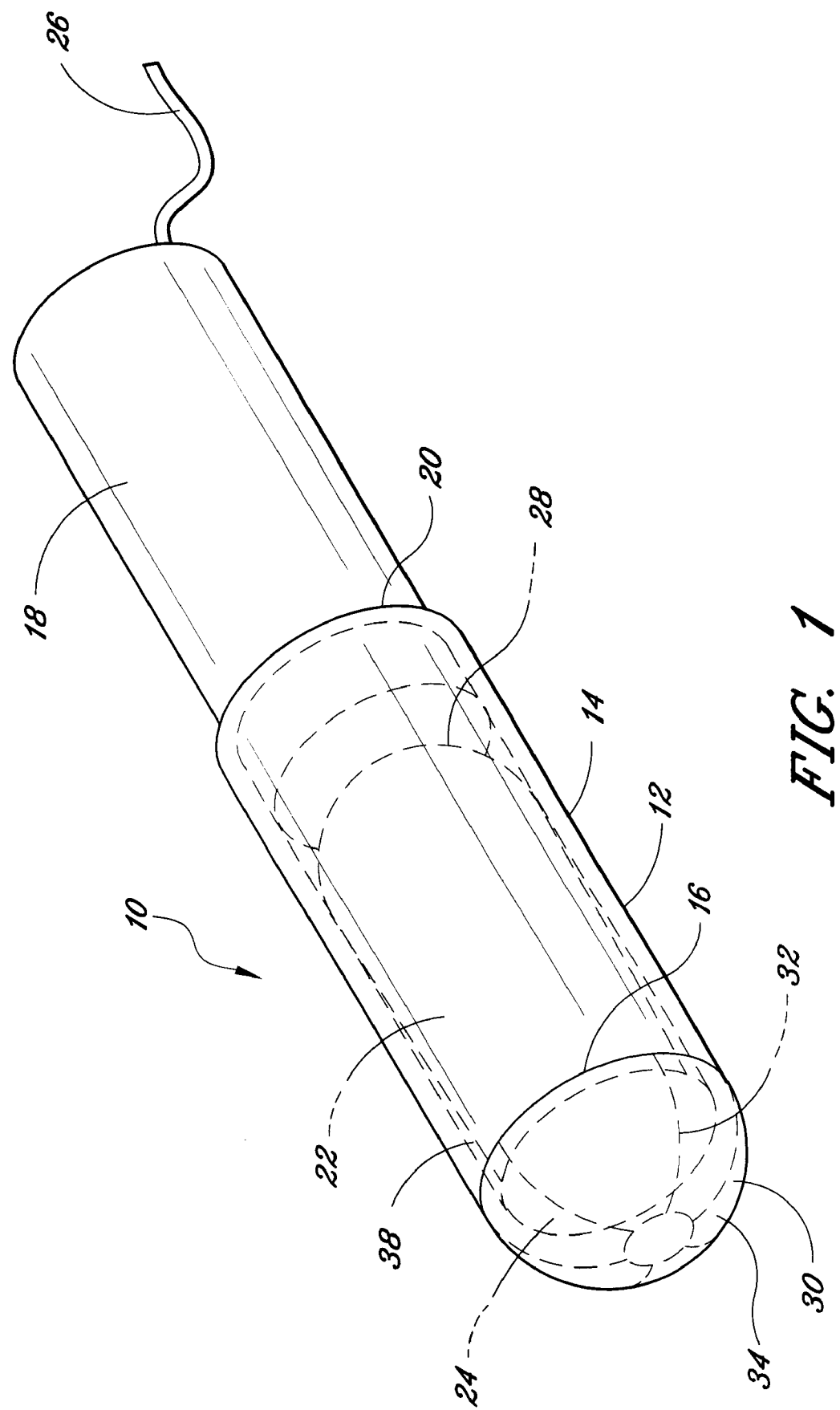

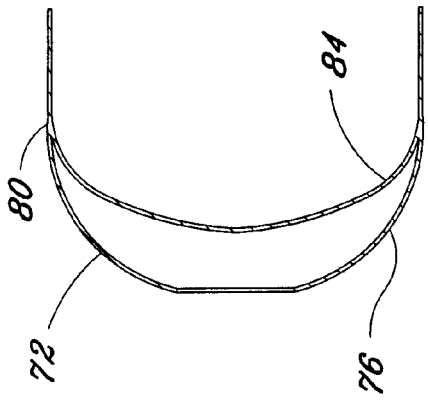
FIG. 7A
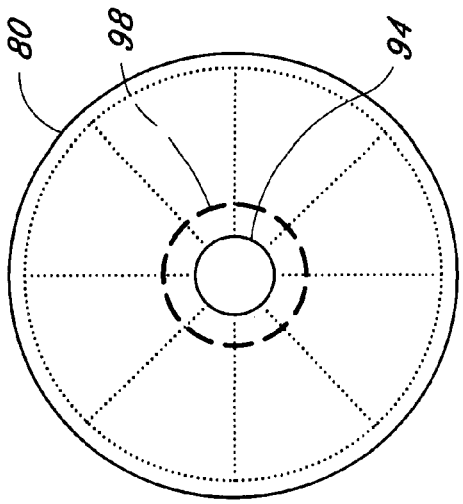
FIG. 7B
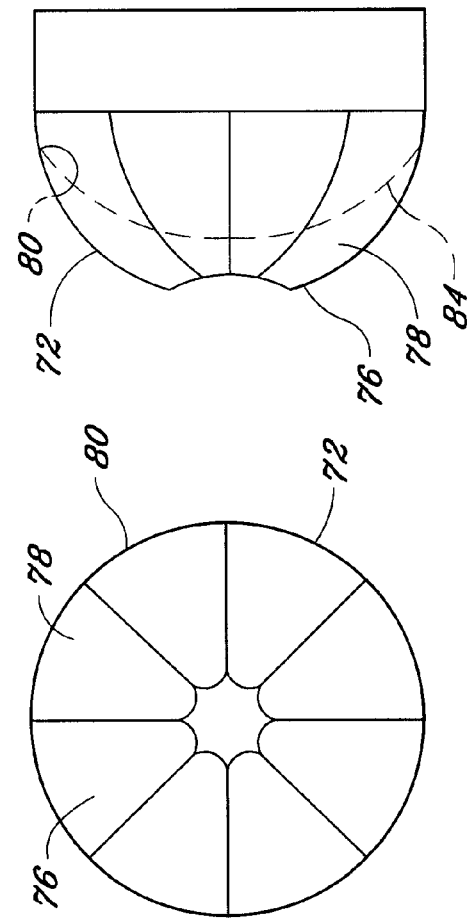
FIG. 7C
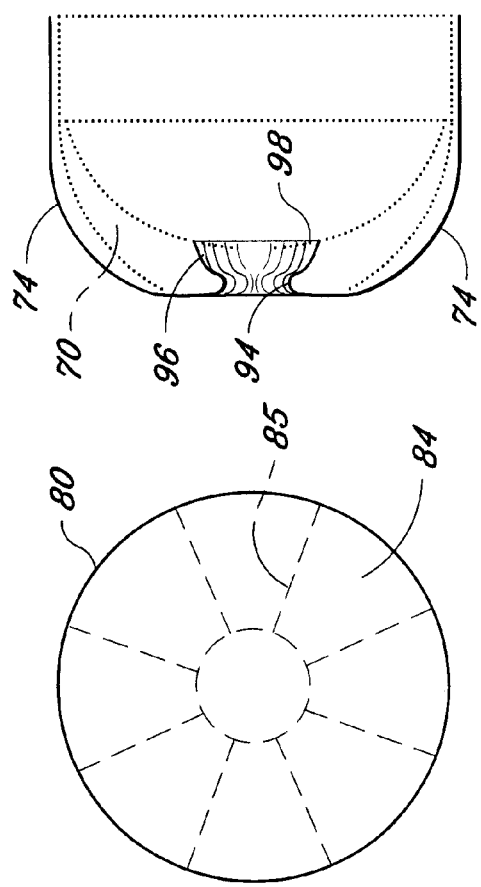
FIG. 7D
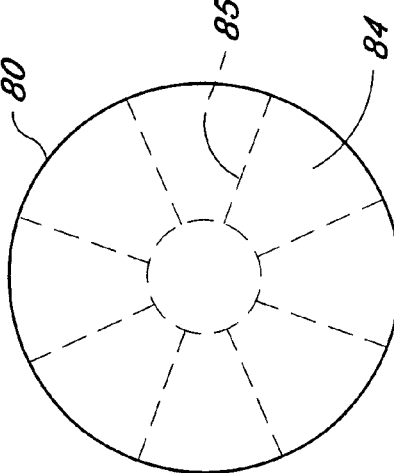
FIG. 7E
FIG. 7F

LUBRICATED TAMPON

CROSS-REFERENCE TO RELATED APPLICATION

This application claims the benefit of U.S. Provisional Patent Application Serial No. 60/222,606, filed Aug. 2, 2000.

BACKGROUND OF THE INVENTION

1. Field of the Invention

The present invention relates to catamenial absorption devices, and, more particularly, to a tampon applicator providing lubrication to the applicator and/or the tampon itself.

2. Description of Related Art

Because of the dry nature of the cutaneous area of the vulva and the labial folds, a lubricated tampon is desirable for comfort and ease of insertion and removal of the tampon from the body cavity. Previous lubricated tampon applicators have had shortcomings in that these devices either are not designed to provide lubrication to both the exterior of the applicator and the tampon itself, or do so inadequately. It is regarded as desirable to provide a disposable tampon and tampon applicator for ease in insertion when there is inadequate liquid or bodily fluid present to lubricate the applicator and/or tampon.

U.S. Pat. No. 2,734,505, issued Feb. 14, 1956 to Parrish, U.S. Pat. No. 3,428,044, issued Feb. 18, 1969, to Whitehead et al., U.S. Pat. No. 3,595,236, issued Jul. 27, 1971, and U.S. Pat. No. 3,724,465, issued Apr. 3, 1973 to Duchane, each describe a dry lubricant coating for a tampon. It requires moisture from the vagina, which may not be available, and time to dissolve the dry lubricant for these lubricants to be useful. Both time and moisture may be limited when inserting a tampon. The present invention provides an applicator capable of effectively lubricating its outer surface and the entire tampon, itself, with a gel-type lubricant during the insertion process.

U.S. Pat. No. 3,139,886, issued on Jul. 7, 1964 to Tallman, describes a lubrication feature for the outside surface of a tampon applicator. In one embodiment packets of lubrication are manually squeezed into the tip of the tampon and then the empty lubrication container removed before insertion. While more effective at delivering lubrication to the tip of the tampon, much of the lubrication will slide down the applicator upon contact with the vagina walls during insertion. Only a small proportion of lubricant would be available to coat the tampon when expelled from the applicator. The present invention delivers most or all of the lubricant to the dry tampon when it is being expelled from the applicator, it presents a smooth, rounded surface at the tip of the applicator during insertion into the vagina, and less refuse in hand is generated, compared to the '886 design which generates caps and empty lubrication containers which must be handled during the insertion process.

U.S. Pat. No. 3,335,726, issued Aug. 15, 1967 to Maranto, describes a device capable of delivering lubrication to the tip of a tampon when expelled from the applicator, but fails to provide for controlled application of lubricant to the entire tampon. No provision is made for lubrication of the outside wall of the applicator. The present invention provides an applicator capable of effectively lubricating the entire tampon with a gel-type lubricant during the insertion process.

U.S. Pat. No. 3,390,671 issued Jul. 2, 1968 to Hildebrand, describes a tampon applicator having a dried lubricating coating. As discussed above, such as in the '505 patent to Parrish, this design requires moisture from the vagina, which may not be available. No provision is made for lubrication of the tampon, itself. The present invention provides an applicator capable of effectively lubricating the entire tampon, itself, with a gel-type lubricant during the insertion process.

U.S. Pat. No. 3,791,385, issued Feb. 12, 1974 to Davis et al. describes a menses collector for insertion into the vagina which, upon insertion form an egg shaped tampon having valves, ridges and impermeable membranes. A lubricant is provided within a removable tip, which may be effective to lubricate the applicator, but would not effectively lubricate the tampon collector device. The present invention provides an applicator capable of effectively lubricating the entire tampon, itself, with a gel-type lubricant during the insertion process.

U.S. Pat. No. 4,421,504, issued Dec. 20, 1983 to Kline, L. H., describes an applicator for injecting a suppository into a body cavity such as the rectum or vagina. The device appears to provide large amounts of lubricant which would be impractical in a tampon insertion applicator, and it is necessarily a relatively expensive device having an O-ring, and also appears to be non-disposable. The present invention is relatively inexpensive and its components are readily disposable. The present invention provides an applicator capable of effectively lubricating the entire tampon with a gel-type lubricant during the insertion process.

U.S. Pat. No. 4,428,747, issued Jan. 31, 1984 to Friese et al., describes a blister package containing a tampon and a separately stored lubricant. No insertion device is provided. The user must manually dip the tampon into the lubricant. The present invention provides an applicator capable of effectively lubricating the entire tampon, itself, with a gel-type lubricant during the insertion process.

U.S. Pat. No. 4,690,671, issued Sep. 1, 1987 to Coleman et al., provides a lubricant or medication reservoir at the upper tip of the applicator and provides for passageways to carry the material along the sides of the tampon and to the opposite end. A protective cap, which must be removed, covers the reservoir. The reservoir is then manually squeezed to inject the material and then removed and discarded. There is no provision for lubrication of the exterior of the applicator, itself. This device requires several steps to be taken by the user, and leaves several separate elements to dispose of. The present invention provides an applicator capable of effectively lubricating the entire tampon with a gel-type lubricant during the simple insertion process, leaving a minimum of separate elements to dispose of. German Patent No. 2,244,586, published Sep. 12, 1972, describes a flat tampon encased in Vaseline® or gelatin that dissolves at body temperature to provide lubrication. Hydrophobic compounds such as Vaseline would inhibit the absorption of the tampon, while dry, hydrophilic compounds such as gelatin would not readily be lubricated at insertion. No applicator is provided. The present invention provides an applicator capable of effectively lubricating the entire tampon with a gel-type lubricant during the insertion process.

Japanese Patent No. 4-322647, issued Nov. 12, 1992, appears to describes a compound, three-part tampon applicator device for placing a tampon in a specified position within a vagina. No provision for lubrication is apparent. The present invention provides an applicator capable of effectively lubricating the entire tampon with a gel-type lubricant during the insertion process.

None of the above inventions and patents, taken either singly or in combination, is seen to describe the instant invention as claimed.

SUMMARY OF THE INVENTION

In accordance with the invention a system is provided to completely lubricate a tampon, and a sanitary wrapper is provided to lubricate the applicator body and insure sterility of the system. The applicator body comprises a tubular-like body in which the tampon is stored, and to which is permanently affixed a lubrication cell near its insertion end. The lubrication cell is scored in such a manner as to preferentially fail in a controlled manner; first the interior cell membrane, and then the exterior cell membrane as the tampon is expelled from the applicator. The tampon is uniquely configured as an integral component of the system, with a lesser circumference about the leading portion than the trailing portion, thereof.

In another embodiment, the lubrication cell features a plastic frame with an elastic membrane stretched over the frame and located at the insertion end of the applicator body similar to the embodiment above. The anterior surface of the plastic frame is prestressed with scoring to facilitate membrane rupture from the force of the ejecting tampon. The forward surface of the plastic frame consists of an open structure with little or no adhesions between adjoining petals. The edges of the frame's petals are all rounded with no sharp corners present. This forward surface forms a frame over which an elastic membrane is secured and defines a hemispherical form for the front of the device. The plastic frame should be formed from a thin thermoplastic such as polyvinyl chloride(PVC).

The elastic membrane is sealed to the tubular body on the exterior and the open end is slightly rolled back upon itself at it-anterior end to provide strength and define the tampon exit point. This end of the elastic membrane is inverted and tucked into the interior of the plastic frame flush against the anterior surface of the plastic membrane, thus assuming the general form of an axially truncated toroid. The configuration of the elastic membrane defines an annular shaped reservoir for the lubrication gel. The elastic membrane presents a slick, smooth surface to the tampon user during all phases of applicator use-applicator insertion, tampon ejection and applicator removal. In addition to providing isolation from the plastic frame, the elastic membrane performs a squeegee action on the tampon all along its surface. Since the cell structure is an open system, the lubricated sanitary wrapper described below is mandatory. The elastic membrane would be made of either latex or a hypoallergenic material such as PVC. The sanitary wrapper is provided having two pieces of paper sealed about the edges with the wrapper portion containing the applicator tip coated on the interior to contain the lubricant. A nonpermanent adhesive bonds the wrapper to the applicator, effectively containing the lubricant. Paper pull-tabs are included to facilitate the opening of the wrapper.

Accordingly, it is a principal object of the invention to provide a tampon and applicator system which is lubricated to eliminate the irritation to the delicate mucus membranes of the vagina caused by insertion and removal of the tampon and applicator.

It is another object of the invention to provide a tampon and applicator system which is economical and simple in design.

It is a further object of the invention to provide a tampon and applicator system which evenly coats the tampon with lubricant on all surfaces to facilitate both insertion and removal.

Still another object of the invention is to provide a tampon and applicator system which lubricates the tampon automatically upon insertion without additional steps in the insertion process.

It is yet another objective of the present invention to provide a tampon and applicator system which minimizes the amount and variety of refuse generated and handled during insertion.

It is still another objective of the present invention to provide a tampon and applicator system having components made from biodegradable materials.

It is yet another objective of the present invention to provide a tampon and applicator system having a smooth, hemispherical tip on the applicator for ease of insertion into the vagina.

It is still another objective of the present invention to provide a tampon and applicator system capable of applying an absolute minimum of hypoallergenic lubricant on the tampon to minimize interference with the tampon's absorbency.

It is yet another objective of the present invention to provide a tampon and applicator system having a lubrication cell so configured as to minimize the force required to release lubricant during application.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is an environmental, perspective view of a lubricated tampon and applicator system according to the present invention, excluding the rear membrane.

FIG. 7A is a detail view of the front of the plastic frame of FIG. 5.

FIG. 7B is a detail view of the side of the plastic frame of FIG. 1.

FIG. 7C is a detail cross section view of the plastic frame of FIG. 5.

FIG. 7D is a detail front view of the posterior wall of the plastic frame of FIG. 5 with the front removed showing the rupture lines.

FIG. 7E is a detail side view in cross section of the elastic membrane of FIG. 5.

FIG. 7F is a detail front view of the elastic membrane of FIG. 5.

Similar reference characters denote corresponding features consistently throughout the attached drawings.

DETAILED DESCRIPTION OF THE PREFERRED EMBODIMENTS

Figure 2A:
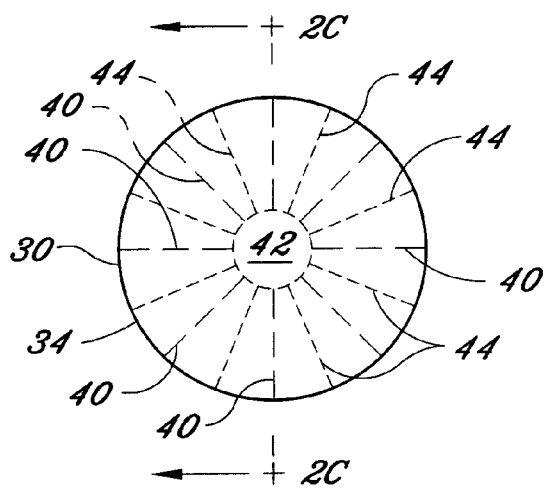
FIG. 2A presents a front detail view of the lubrication cell of FIG. 1 showing groove patterns in front and rear membranes.

The present invention is a system which is provided to completely lubricate a tampon, including a sanitary wrapper provided to lubricate the applicator body and insure sterility of the system. The applicator body comprises a tubular-like body in which the tampon is stored, and to which is permanently affixed a lubrication cell near its insertion end. The lubrication cell is scored in such a manner as to preferentially fail in a controlled manner; first the interior cell membrane, and then the exterior cell membrane as the tampon is expelled from the applicator. The tampon is uniquely configured as an integral component of the system, with a lesser circumference about the leading portion than the trailing portion, thereof.

In another embodiment an elastic membrane is sealed to the tubular body on the exterior and the open end is slightly rolled back upon itself at its-anterior end to provide strength and define the tampon exit point. This end of the elastic membrane is inverted and tucked into the interior of the plastic frame flush against the anterior surface of the plastic membrane, thus assuming the general form of an axially truncated toroid(similar to a sliced bagel). The configuration of the elastic membrane defines an annular shaped reservoir for the lubrication gel. The forward surface of the plastic frame consists of an open structure with little or no adhesions between adjoining petals. The edges of the frame's petals are all rounded with no sharp corners present. This forward surface forms a frame over which an elastic membrane is secured and defines a hemispherical form for the front of the device.

A sanitary wrapper is provided having two pieces of paper sealed about the edges with the wrapper portion containing the applicator tip coated on the interior to contain the lubricant. A nonpermanent adhesive bonds the wrapper to the applicator, effectively containing the lubricant. Paper pull-tabs are included to facilitate the opening of the wrapper.

Referring to FIG. 1, tampon system 10 is shown in an environmental perspective view without the wrapper. Tampon system 10 features tampon applicator case 12 including tampon insertion cylindrical case 14 having cylindrical case front end 16, insertion plunger 18 being partially inserted into cylindrical case 14 at cylindrical case rear end 20. Tampon 22 is stored within cylindrical case 14 and features tampon hemispherically shaped front end 24 and tampon retrieval string 26 attached to tampon 22 at tampon rear end 28. Lubricant cell 30 is hemispherically shaped and is attached around its perimeter to cylindrical case front end 16 so as to make a smooth transition from lubricant cell 30 to insertion cylinder 14. Lubricant cell 30 incorporates inner wall membrane 32 (shown in FIGS. 2A–2D) and outer membrane wall 34, sealed at its perimeter to encase an appropriate lubricant. Annular lubrication gap 38 is defined by tampon 22 and insertion cylinder 14 and provides a conduit to receive lubrication from lubrication cell 20 upon deployment of the tampon system 10. Tampon 22 has a slightly smaller diameter near its front end 24 and is tapered to a larger diameter conforming with the inside diameter of the tampon insertion cylinder 14 at a point about three-quarters along the length of the tampon 22 from the front end 24.

Referring to FIG. 2A there is shown a front detail view of the lubrication cell 30 showing the lubrication cell outer wall 34 and featuring eight prestressed failure grooves 40 distributed evenly around the outer wall 34 and meeting in centrally located outer central cell surface 42. Also shown are the eight prestressed failure grooves 44 of lubrication cell inner wall 32, and which are rotated 22½ degrees relative to failure grooves 40 to assist in assuring their sequential rupture as discussed below.

Figure 2B:
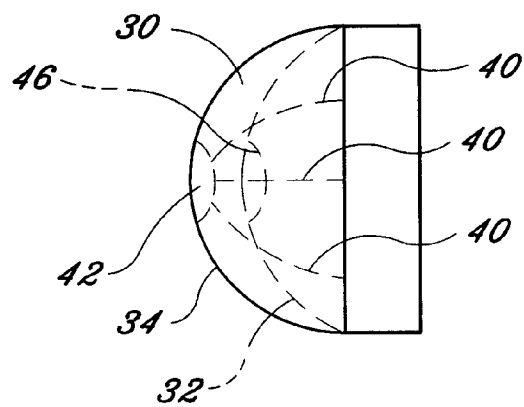
FIG. 2B presents a side detail view of the lubricating cell of FIG. 1.
Figure 2C:
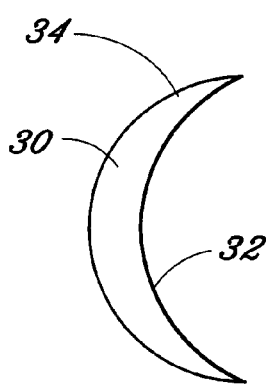
FIG. 2C presents a side sectional view of the lubricating cell of FIG. 1A.

FIG. 2B is a side detail view of the lubrication cell 30, showing lubrication cell outer wall 34 and inner wall 32. FIG. 2C is a sectional view along lines 2C—2C of FIG. 2A showing the crescent-shaped cross section of lubrication cell 30 along a plane which includes a central axis of said insertion cylinder 14 and formed by outer wall 34 and inner wall 32.

Figure 2D:
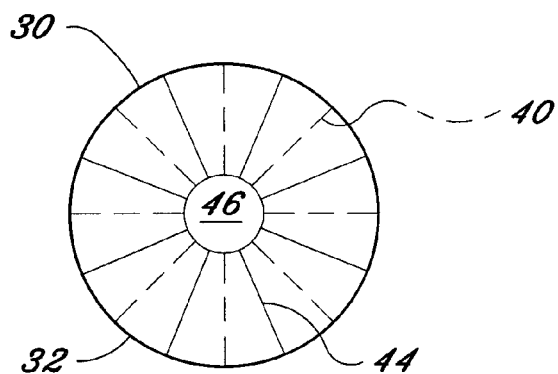
FIG. 2D presents a rear detail view of the lubrication cell of FIG. 1.

FIG. 2D is a rear view of the lubrication cell 30 showing inner cell surface 32 featuring eight prestressed failure grooves 44, meeting at inner central cell surface 46. Also shown in phantom are prestressed failure grooves 40 of outer cell surface 34 as describe above in the discussion of FIG. 2A.

Figure 3:
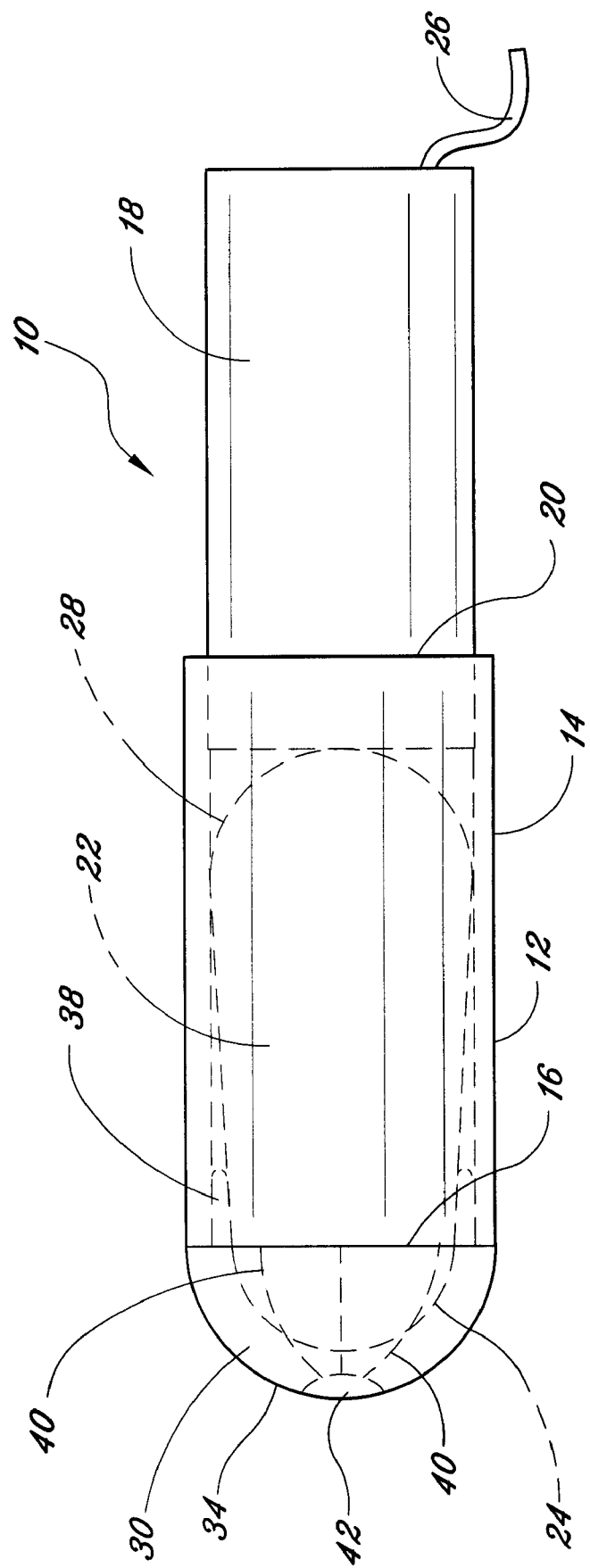
FIG. 3 is a diagrammatic elevation view of the lubricated tampon and applicator system of FIG. 1, illustrating the tampon partially inserted into the lubrication cell.
Figure 4:
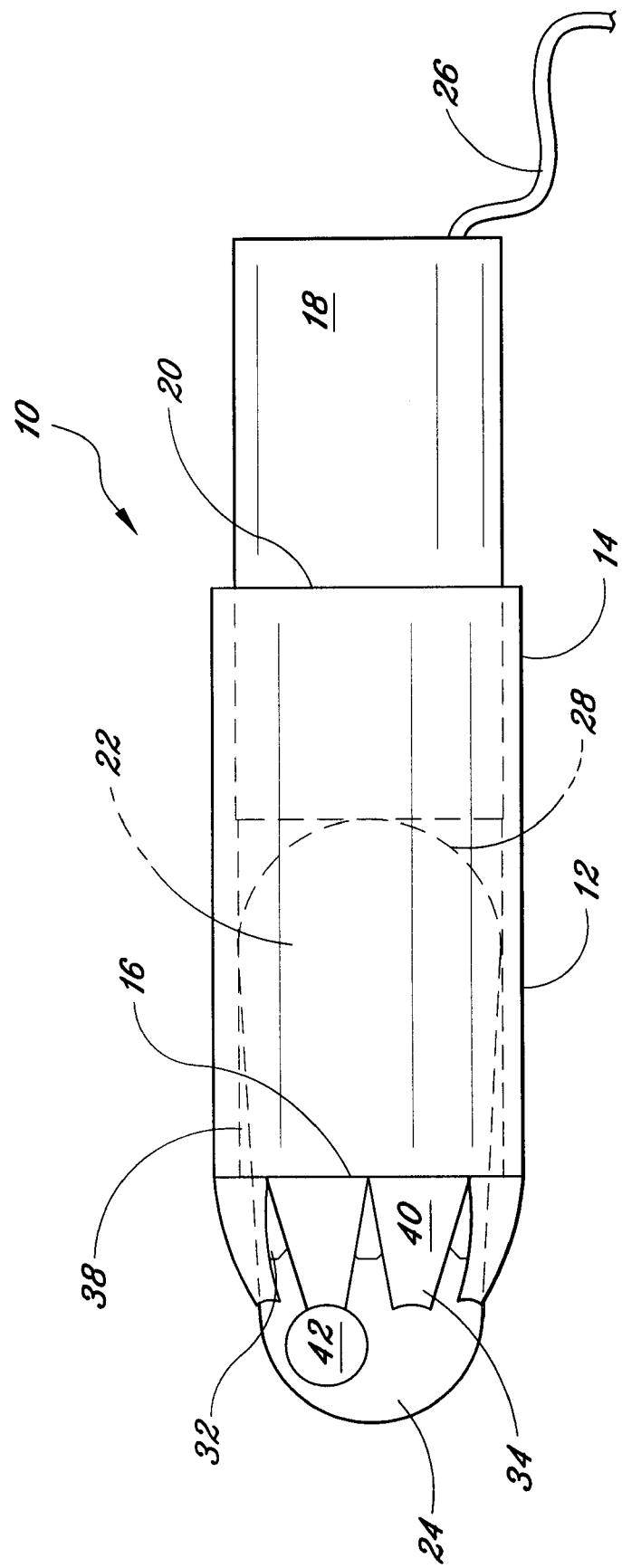
FIG. 4 is a diagrammatic elevation view of the lubricated tampon and applicator system of FIG. 1, illustrating the tampon breaching the entire lubrication cell.

Referring to FIGS. 3 and 4, tampon 22 is deployed by inserting lubrication cell 30 and insertion cylinder 14 into the vagina. As seen in FIG. 3, plunger 18 is pressed forward against tampon rear end 28 and into insertion cylinder 14 from its location near cylindrical case rear end 20, driving tampon 22 forward, its front end 24 rupturing lubrication cell 30 at inner wall 32 (not shown). As plunger 18 is pressed further into insertion cylinder 14, tampon front end 24 displaces lubricant held within lubrication cell 30, forcing it into annular lubrication channel gap 38. As seen in FIG. 4, plunger 18 is pressed further forward against tampon rear end 28, driving tampon 22 forward, its front end 24 rupturing lubrication cell outer wall 34. During this time, lubricant forced into annular lubrication gap 38 lubricates the outer surface of tampon 22 as it travels further along insertion cylinder 14. As the tampon continues to be pressed forward by insertion plunger 18, lubrication is spread over the surface of tampon 22 such that upon full deployment, tampon 22 is completely covered by lubricant, thereby achieving the desired result. Portions of lubrication cell inner wall 32 and outer wall 34 remaining after rupture of outer wall membrane 34 maintain contact with the outer surface of tampon 22 to keep the tampon centered so that lubrication is evenly spread over its outer surface and to avoid rupture membrane ends from irritating the vagina wall. Tampon applicator 12 is then withdrawn from the vagina, leaving tampon 22 in place to perform its normal function. It is noted that no separate caps or other debris is produced and the applicator is disposable in one biodegradable piece.

Figure 5:
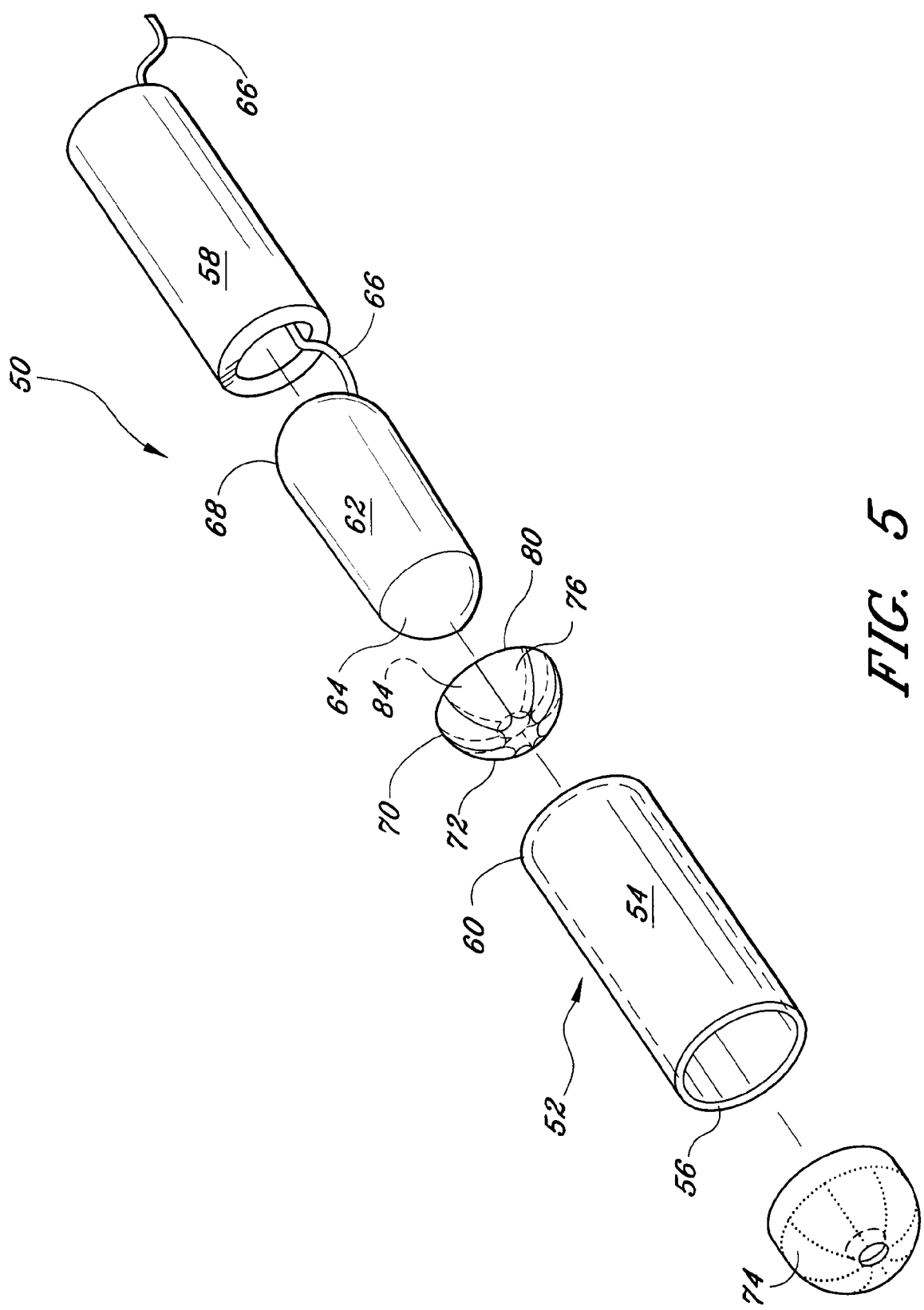
FIG. 5 is an exploded view in perspective of a preferred embodiment of a lubricated tampon of the present invention.

Referring to FIG. 5, a preferred embodiment of the inventive tampon system is generally referred to as tampon system 50, which is configured similarly to tampon system 10 except for the lubrication cell and elastic membrane configuration.

Referring to FIG. 5, tampon system 50 is shown in an exploded view in perspective without the wrapper. Tampon system 50 features tampon applicator case 52 including tampon insertion cylindrical case 54 having cylindrical case front end 56, insertion plunger 58 being partially insertable into cylindrical case 54 at cylindrical case rear end 60. Tampon 62 is stored within cylindrical case 54 and features tampon front end 64, and tampon retrieval string 66 attached to tampon 62 at tampon rear end 68. Lubricant cell 70 features a plastic frame 72 with an elastic membrane 74 stretched over the frame 72. The anterior surface 76 of the plastic frame 70 consists of an open structure having little or no adhesion between adjoining petals 78 which collectively form surface 76. The petals 78 are joined to the plastic frame 72 at its perimeter 80 and the petal edges are each rounded, having no sharp corners present. The anterior surface 76 forms a frame over which elastic membrane 74 is secured and defines a hemispherical form for the front of the device 50. The plastic frame is preferably formed from thin thermoplastic such as PVC. The posterior wall 84 of lubricant cell 70 is similar in configuration to that of the first embodiment (see FIGS. 2D and 7D) and is attached to plastic frame perimeter 80.

Figure 6:
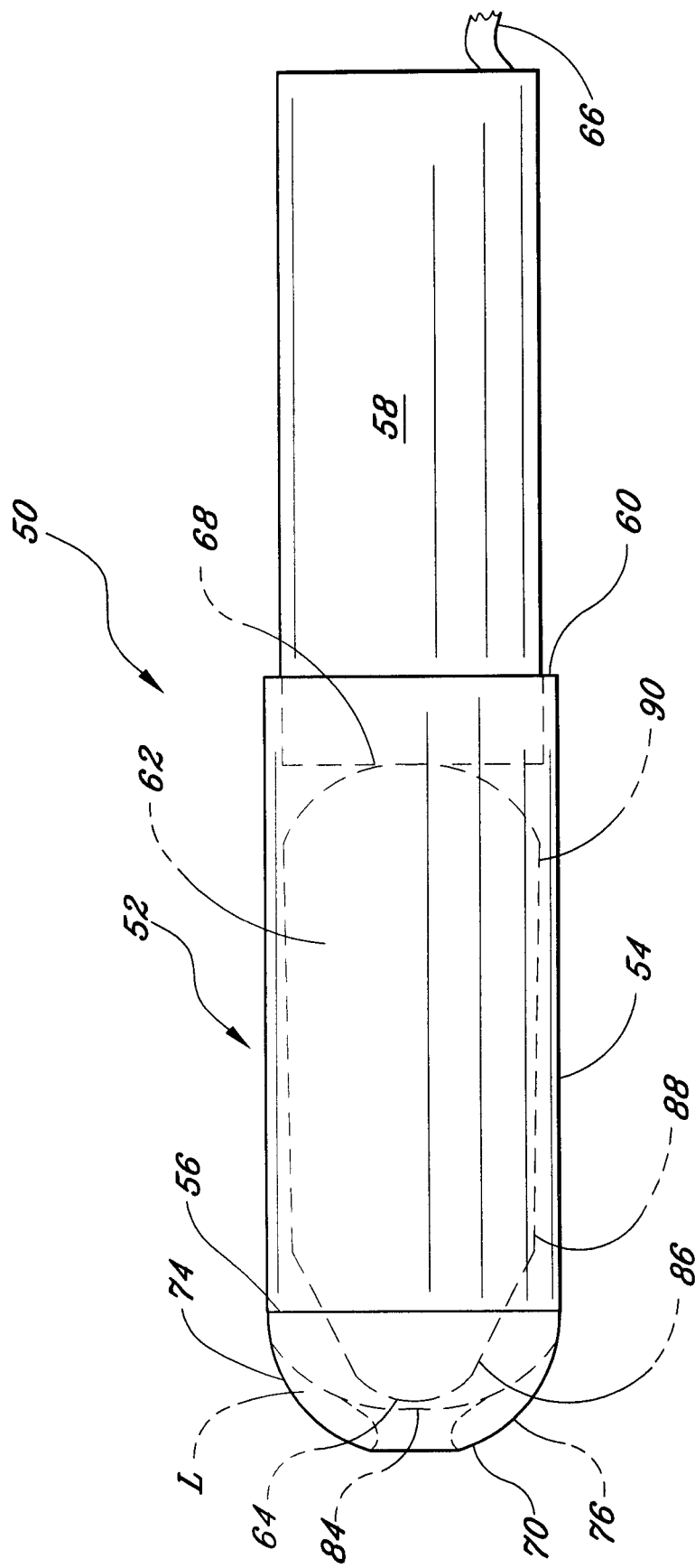
FIG. 6 is a diagrammatic side view in elevation of the embodiment of FIG. 5 in its stored state.

Referring to FIG. 6 there is shown a diagrammatic side view in elevation of the embodiment of FIG. 5 in its assembled, stored state. Tampon system 50 includes tampon applicator case 52 having insertion cylindrical case 54, having front end 56, and insertion plunger 58 partially inserted into cylindrical case 54 through cylindrical case rear end 60. Tampon 62 resides within cylindrical case 54 immediately ahead of insertion plunger 58 and features front end 64 and retrieval string 66 attached at tampon rear end 68. Lubricant cell 70 contains lubricant L features plastic frame 72 (see FIG. 5) covered by elastic membrane 74 covering plastic frame 72. posterior wall 84 remaining intact. Lubricant cell posterior wall 84 is located immediately ahead of tampon front end 64. Tampon 62 has a preferred shape wherein tampon front end 64, the leading surface, is rounded and of much less diameter than that of the remainder. This configuration facilitates the leading portion of the tampon sealing with the elastic membrane 74 and trapping lubricant within the lubricant cell 70. Tampon tapered surface 86 is tapered approximately 30 degrees from the tampon central axis. Tampon tapered lubricating surface 88 extends rearward along the tampon 62 and is tapered approximately 3 to 6 degrees from the central axis. Tampon cylindrical surface 90 is cylindrical in shape and is parallel to the central axis. Tampon rear end 68 has a gently curved surface leading to the central axis and the attachment of retrieval string 66 (not shown).

Referring to FIGS. 7A–7D, there are shown detail views of the plastic frame and lubricant cell of FIG. 5. FIG. 7A is a front view of the plastic frame of FIG. 5 without posterior wall 84, wherein plastic frame 72 has plastic frame anterior surface 76 made up of frame surface petals 78 attached at perimeter 80. FIG. 7B is a side view of the plastic frame of FIG. 5 wherein plastic frame 72 has plastic frame anterior surface 76 made up of frame surface petals 78 attached at perimeter 80. Lubricant cell posterior wall 84 is located within plastic frame 72. FIG. 7C is a cross section view of the plastic frame of FIG. 5 wherein plastic frame 72 has plastic frame anterior surface 76 and posterior wall 84 joined at frame perimeter 80. FIG. 7D is a front view of the plastic frame of FIG. 5 with anterior wall 76 removed, wherein posterior wall 84 has rupture lines 84 extending radially to plastic frame perimeter 80.

Referring to FIGS. 7E and 7F, there are shown a side cross section and a front view, respectively, of the elastic membrane of FIG. 5. FIG. 7E is a side cross section view of elastic membrane 74 wherein lubricant cell 70 is confined within elastic membrane 74 between the plastic frame (diagrammatically shown in dots) and the membrane orifice 94 and membrane inner flare portion 96 ending at inner membrane-lubrication cell posterior wall contact portion 98. FIG. 7F, is a front view of the elastic membrane showing membrane orifice 94 leading to inner membrane-lubrication cell posterior wall contact portion 98 in its central portion and extending around its outer edge over plastic frame perimeter 80 (shown in dots).

Figure 8:
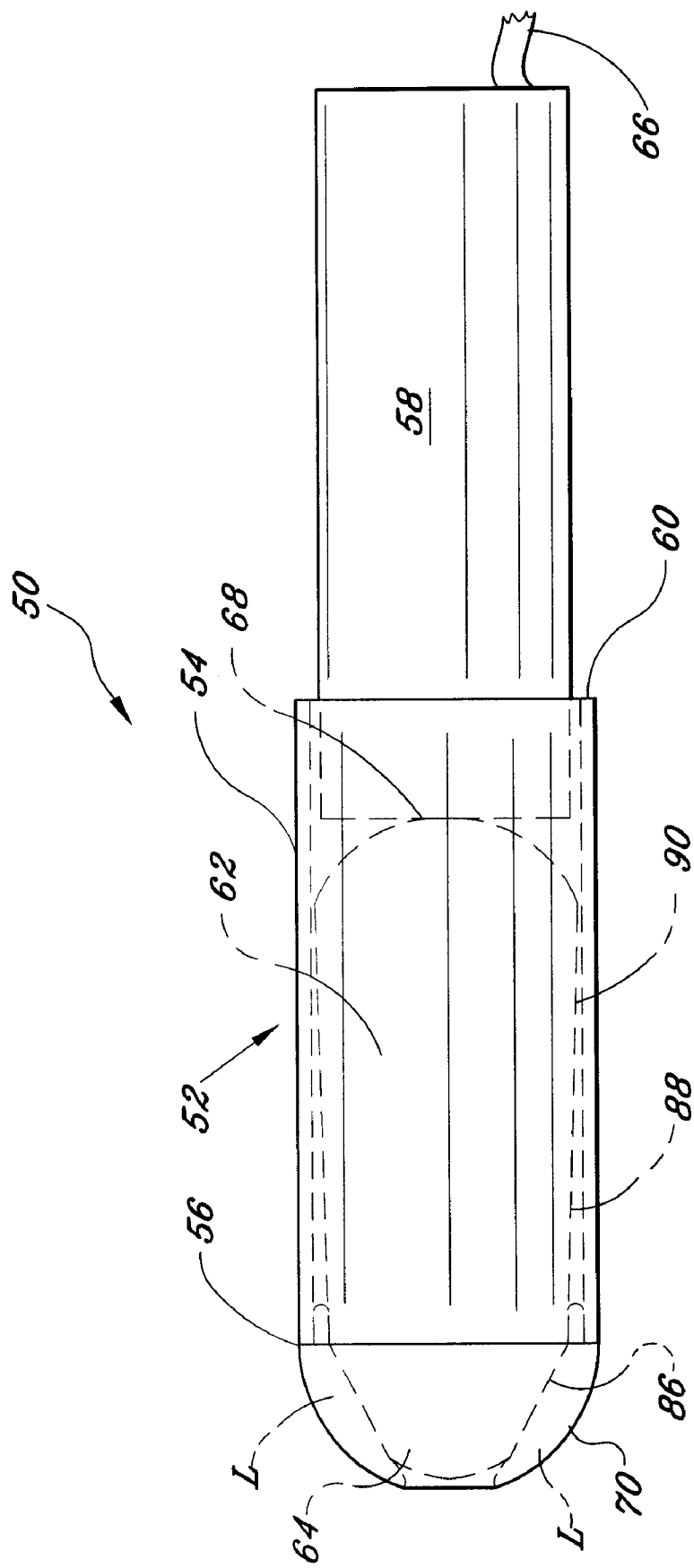
FIG. 8 is a diagrammatic side view in elevation of the embodiment of FIG. 5 with plunger after lubrication cell rupture.

Referring to FIG. 8, there is shown a diagrammatic side view of the embodiment of FIG. 5 with the plunger after lubrication cell rupture. As plunger 58 has traveled forward, tampon front end 64 has now breached lubricant cell posterior wall 84, forcing lubricant L between the inner wall of insertion cylindrical case 54 and tampon tapered lubricating surface 88, thus providing lubrication around the tampon 62.

Figure 9:
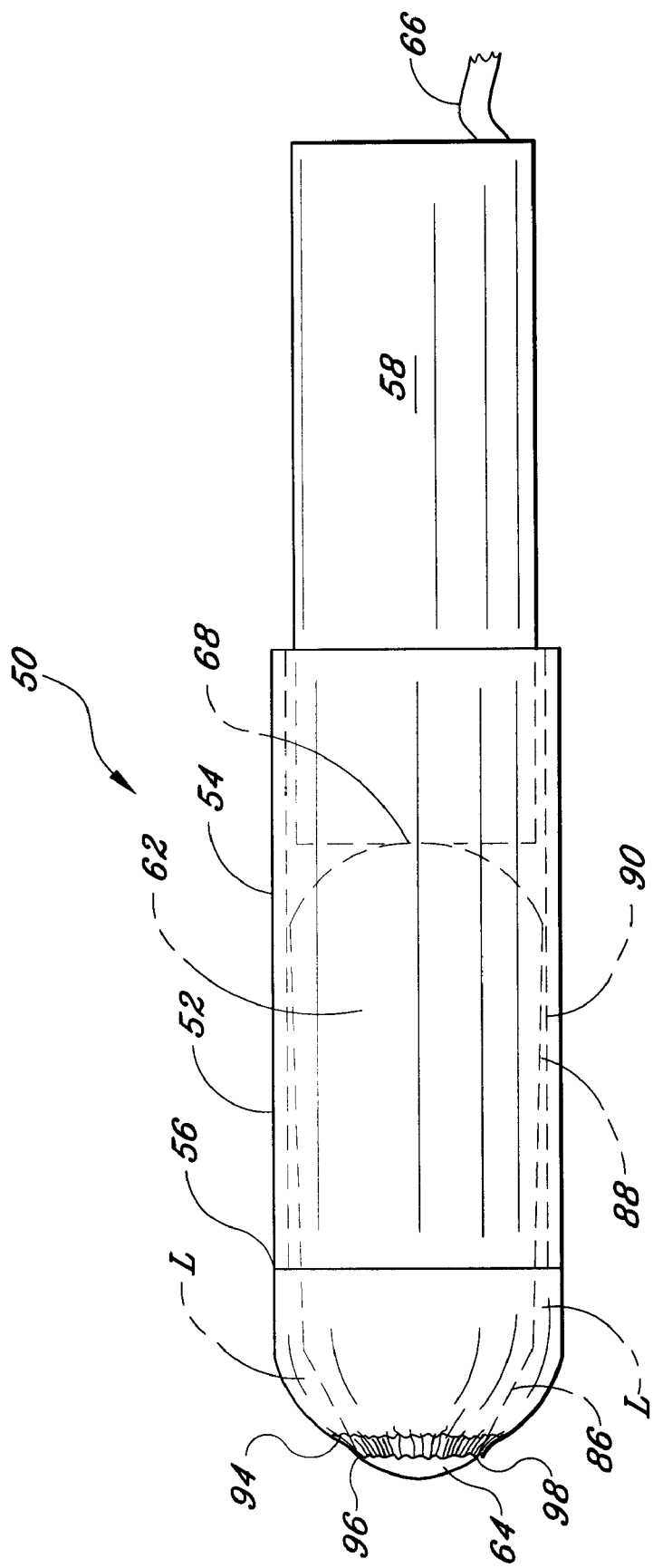
FIG. 9 is a diagrammatic side view in elevation of the embodiment of FIG. 1 with tampon inserted into elastic membrane.

Referring to FIG. 9, there is shown a diagrammatic side view of the embodiment of FIG. 5 with the plunger moved further forward. Plunger 58 has displaced tampon 62 such that tampon front end 64 has pushed elastic membrane wall contact 98 and membrane inner flare portion 96 inside out through an enlarged membrane orifice 94. At the same time, lubricant L is spread further along the tapered surface 88 of tampon 62.

In operation, tampon 62 is deployed by inserting elastic membrane 74, as stretched over plastic frame 72, and insertion cylinder 54 into the vagina. As seen in FIG. 6, plunger 58 is pressed forward against tampon rear end 68 and into insertion cylinder 54 from its location near cylinder rear end 60, driving tampon 62 forward, its front end 64 rupturing lubrication cell 70 at inner wall posterior wall 84 along scored lines 85. A lubricant reservoir is formed between tampon tapered surface 86 and the plastic frame surface petals 78. As the plunger 58 is pressed further, tampon front end 64 bears against elastic membrane 74, pushing membrane inner flare portion 96 out through an expanded membrane orifice 94. Simultaneously, lubricant L is forced between the tapered lubricating surface 88 of tampon 62 and the inner wall of cylindrical case 54, thus lubricating the tampon outer wall as it is pushed further. As the tampon continues to be pressed forward by insertion plunger 58, lubrication is spread uniformly over the surface of tampon 62. Tampon cylindrical surface 90 fits closely inside insertion cylindrical case 54, thus, keeping the tampon traveling straight as it moves forward through the case 54. As the tampon is ejected, lubricant is applied to tampon cylindrical surface 88 and tampon rear end 68 such that upon full deployment, tampon 62 is completely covered by lubricant, thereby achieving the desired result. Tampon applicator 52 is then withdrawn from the vagina, leaving tampon 62 in place to perform its normal function. It is noted that no separate caps or other debris is produced and the applicator is disposable in one biodegradable piece.

Figure 10:
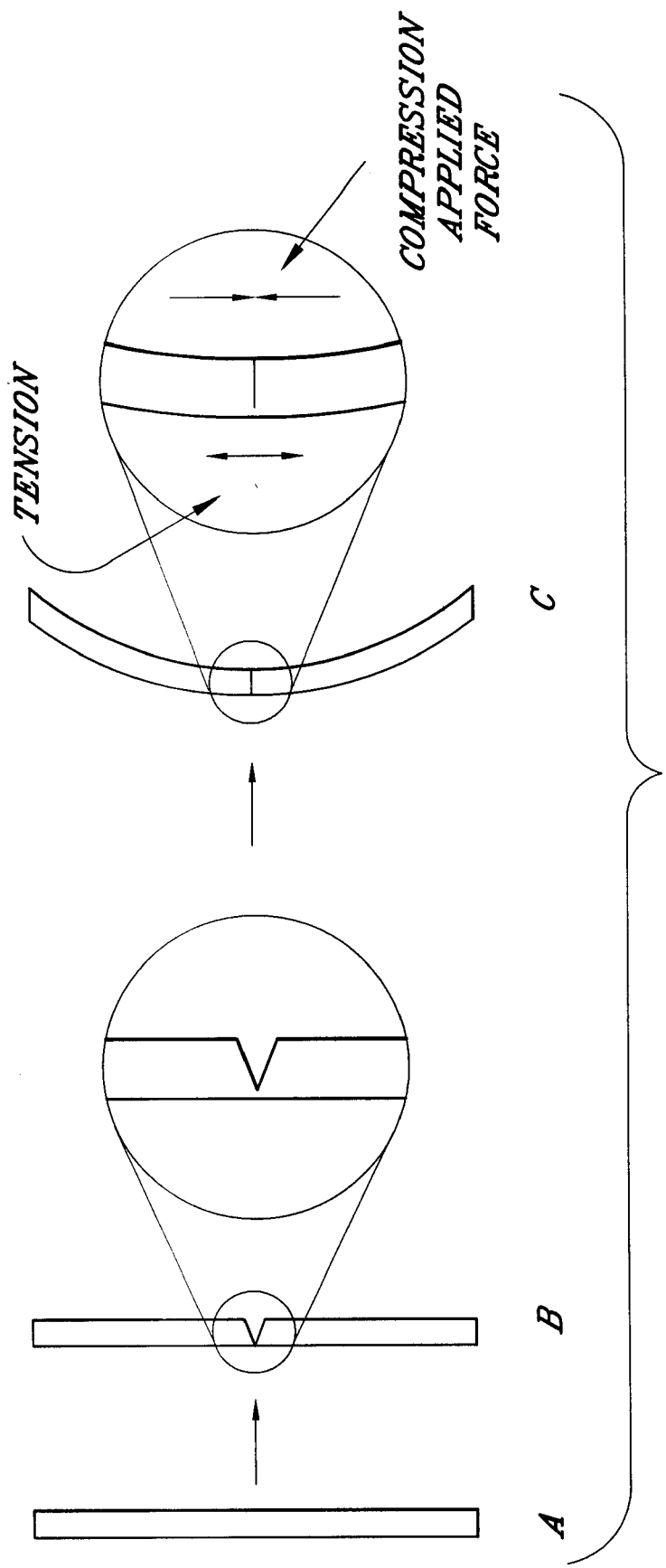
FIG. 10 illustrates the scoring mechanism employed in arcuate cell membranes to assure rupture of the cell in the desired sequence.

Referring to FIG. 10 there is illustrated the technique of membrane scoring which allows for predetermined failure modes in the membranes described above. The scoring of the membrane A is done in such a manner as to create a "V" shaped groove as in step B, which closes when the material is formed into the cells of the desired shape, as in step C, as described above. This creates a moment about the score with compressive forces acting on the surface on one side of the membrane and amplifying tensile forces on the other side to cause failure of the surface. This will allow the scored membrane to be at a reasonable strength to prevent premature rupture from exterior forces, while allowing an absolute minimum of force to rupture it when ejecting a tampon.

Referring to FIGS. 2A–2D and 7A–7D, an interior generally concave membrane surface is preferred to keen the tampon centered as to retain the annular gap evenly between tampon and case for lubricant to migrate through at use. If a thermoplastic is used for the membrane, the membranes may be thermally fused to each other and to the case. Cross section details show this extra membrane material intended to be bonded to the case. A useful material for the membranes is polyethylene or polyvinyl chloride. It is preferred that a small amount of a compressible gas, such as air, be included within the above-described lubricant cell of FIGS. 2A–2D so as to facilitate the sequential breaching of the inner and outer walls, respectively, as described above. A gel-type nonirritating lubricant such as K-Y Liquid® by Ortho-McNeil Pharmaceutical, Inc. is preferred as the lubricant filling the various described lubrication cells. An equivalent lubricant is Vagisil®.

Figure 11:
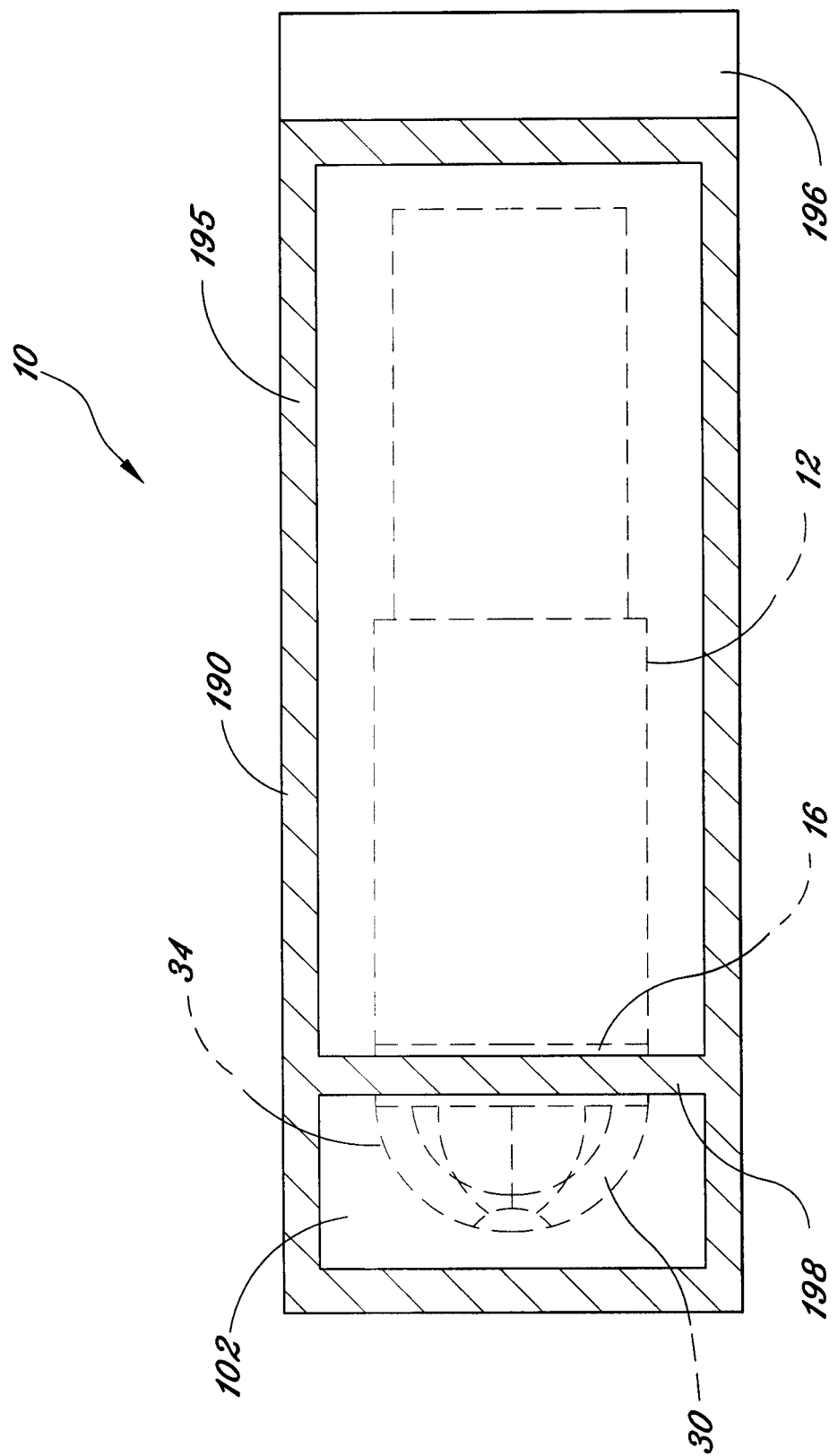
FIG. 11 is a diagrammatic plan view of the wrapper of the lubricated tampon system of FIG. 1.
Figure 12:
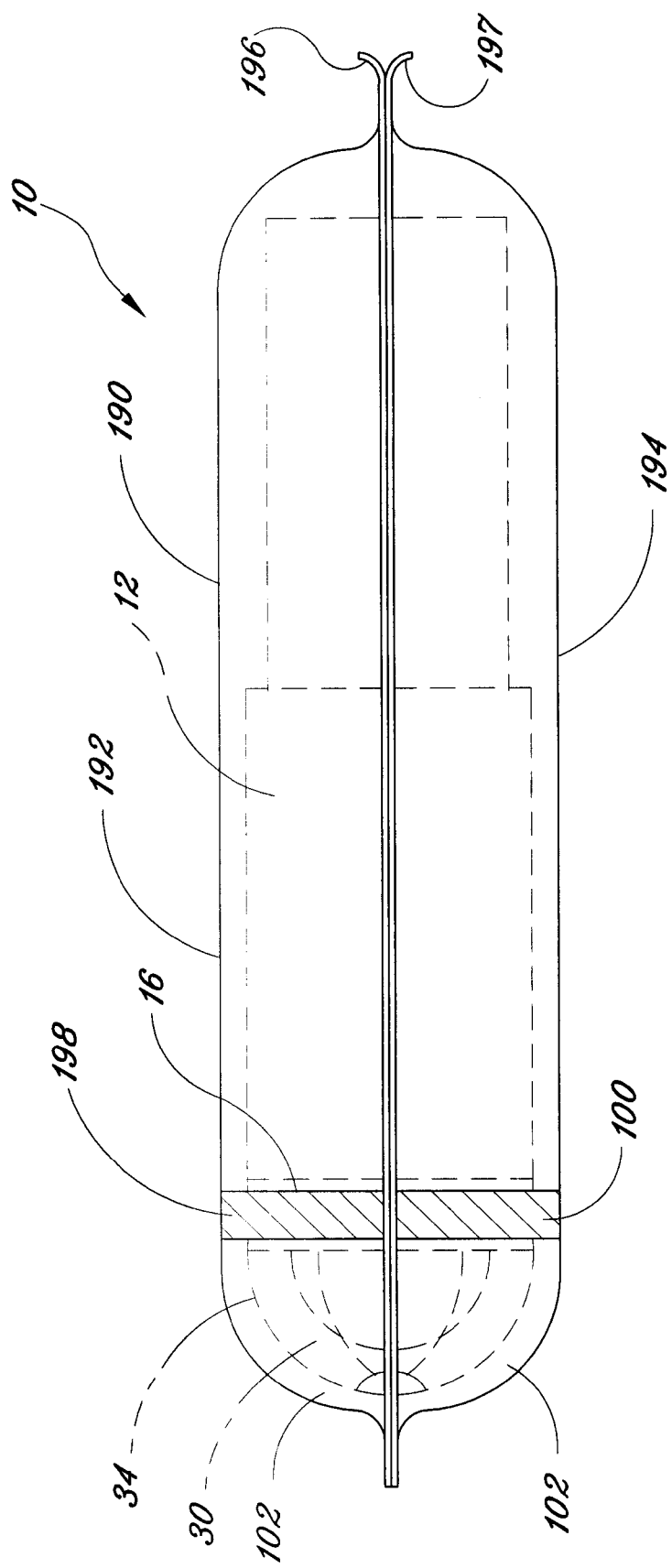
FIG. 12 is a diagrammatic side view of the wrapper of the lubricated tampon system of FIG. 1.

Referring to FIGS. 11 and 12, there is shown a plan view and an elevation view, respectively, of the inventive tampon system within a sanitary wrapper with encased lubrication to insure that the exterior of the tampon applicator of the present invention is lubricated before use. Tampon system 10 is shown with tampon applicator 12 encased in sanitary wrapper 190 having a lubricated area to cover the tip of the encased tampon. The wrapper is preferably constructed from two adjoining upper and lower portions 192 and 194 with surrounding edges 195 sealed around the perimeter of the tampon applicator 12 with an adhesive amenable to separation upon being subjected to peeling force. The rear portion of the sanitary wrapper relative to the tampon is provided with free pull tabs 196 and 197 so as to enable the user to quickly breach the wrapper 190 and peel it away. Inner adhesive strips 198 and 100 are located at corresponding locations along the inner wall of upper and lower portions 192 and 194, respectively, so as to adhere to the front end portion 16 of tampon insertion cylinder 14, to form lubrication pocket 102, said adhesive being of a type forming a bond which is easily breached under peeling force. Lubrication pocket 102 contains a predetermined amount of gel-type lubricant, such as K-Y Jelly® to maintain the outer wall 34 of the lubrication cell 30 in a lubricated condition for easy use. The wrapper material is preferably of a waterproof material, particularly within the lubricated area 102, and may be constructed of layered plastic coated paper or the like. This sanitary wrapper 190 is useful for both the embodiment of FIG. 1 and that of FIG. 5.

It is to be understood that the present invention is not limited to the embodiments described above, but encompasses any and all embodiments within the scope of the following claims.

I claim:

1. A lubricated tampon system having an applicator comprising:
   a) a cylindrical casing having a front end and a rear end and a generally constant circumference;
   b) a generally cylindrical tampon having a front end and a rear end, said tampon being located within said cylindrical casing and tapering inwardly from the rear end to the front end from a point about one-quarter of the way from said rear end, thus defining an annular void between said tampon and said cylindrical casing in the vicinity of said front end of said cylindrical casing;
   c) an insertion plunger slidable through said rear end of said cylindrical casing and extending therein to a point adjacent said rear end of said tampon;
   d) a retrieval string attached to the rear end of said tampon; and
   e) a lubrication cell containing a lubricant and a compressible gas and located at said front end of said casing and attached around said circumference, thereof, said lubrication cell comprising:
      1) a front hemispheric membrane having an outer side and an inner side and a perimeter, and projecting forward of the front end of said casing and having a series of scores on said inner side, thereof, so configured as to selectively fail at a first pressure level applied in an outward direction from said cylindrical casing; and
      2) a rear hemispheric membrane having an inner side and an outer side and a perimeter, and projecting forward of said casing front end and sealed around its perimeter to the perimeter of said front membrane and having a series of scores on said inner side, thereof, relative to said cylindrical casing, said front membrane and said rear membrane forming said lubrication cell, said scores being so configured as to allow integral failure of said rear membrane at a second pressure applied in an outward direction from said cylindrical casing, said second pressure being less than said first pressure.

2. The lubricated tampon system of claim 1, wherein a cross section of said lubrication cell along a plane containing the central axis of said cylindrical casing forms a crescent.

3. The lubricated tampon system of claim 1, wherein said front membrane comprises an outer central cell surface, and wherein said second membrane comprises an inner central cell surface.

4. The lubricated tampon system of claim 3, wherein said scores comprise a plurality of radially oriented scores and a circular outer central score defining said outer central cell surface, said radially oriented scores emanating from said central cell surface and extending to said perimeter.

5. The lubricated tampon system of claim 4, wherein said rear membrane scores comprise a plurality of radially oriented scores and a circular outer central score defining said outer central cell surface, said radially oriented scores emanating from said outer central cell surface and extending to said perimeter.

6. The lubricated tampon system of claim 5, wherein said rear membrane radially oriented scores form a plurality of generally triangular surfaces relative to said periphery and said front membrane radially oriented scores are rotated relative to said rear membrane such as to bisect each of said generally triangular surfaces.

7. The lubricated tampon system of claim 6, wherein each of said rear membrane radially oriented scores and said front membrane radially oriented scores are eight in number, respectively.

8. The lubricated tampon system of claim 1, further comprising a sanitary wrapper encasing said tampon applicator.

9. The lubricated tampon system of claim 8, wherein said sanitary wrapper comprises two adjoining upper and lower portion with surrounding edges seal around the perimeter of said tampon applicator.

10. The lubricated tampon system of claim 9, wherein said sanitary wrapper has a rear portion relative to said tampon having two free pull tabs so as to promote the quick breach of the sanitary wrapper for separation by peeling.

11. The lubricated tampon system of claim 9, wherein said sanitary wrapper comprises upper and lower inner adhesive strips so positioned as to adhere to said front end portion of said applicator cylinder, forming a lubrication pocket for containing lubrication therein.

12. A lubricated tampon system having a generally cylindrical applicator comprising:
   a) a cylindrical casing having a front end and a rear end and a generally constant circumference;
   b) a generally cylindrical tampon having a front end, a central portion, and a rear end, said tampon being located within said cylindrical casing and tapering inwardly from said rear end and said front end from a point about one-quarter of the way from said rear end, thus defining an annular void between said tampon and said cylindrical casing in the vicinity of said front end and said central portion of said cylindrical casing;
   c) an insertion plunger slidable through said rear end of said cylindrical casing and extending therein to a point adjacent said rear end of said tampon;
   d) a retrieval string attached to said rear end of said tampon;
   e) a plastic cage having a cell containing a lubricant and located at said front end of said casing and attached around said circumference, thereof, said plastic cage comprising:
      1) a rear hemispheric membrane having a prestressed scored outer side and an inner side, and a perimeter, and projecting forward of said casing front end, said scored outer side allowing said membrane to be breached by a given outer directed pressure from said tampon front end; and
      2) a front generally hemispheric structure projecting forward of the front end of said casing and comprising a plurality of petals extending from said perimeter and terminating as outer edges; and
   f) an elastic membrane stretched over and substantially covering said plastic frame and having a centrally located membrane orifice, a membrane inner flare portion extending inward from said orifice and flaring outward, and an inner membrane-lubrication cell posterior wall contact portion which abuts and seals against said posterior wall;
   said rear membrane, said petals and said elastic membrane forming a lubrication cell containing lubrication for said tampon.

13. The lubricated tampon system of claim 12, wherein the outer edges of said petals are rounded, defining a generally circular scalloped aperture.

14. The lubricated tampon system of claim 13, wherein said elastic membrane orifice extends inward through said scalloped aperture, said flared portion extending generally radially outward to seal against said rear membrane at said contact portion.

15. The lubricated tampon system of claim 14, wherein said tampon comprises in order a rounded front end portion, a tampon tapered surface portion, a tapered lubricating surface portion, a tampon cylindrical surface portion and a rounded end portion.

16. The lubricated tampon system of claim 12, further comprising a sanitary wrapper encasing said tampon applicator.

17. The lubricated tampon system of claim 16, wherein said sanitary wrapper comprises two adjoining upper and lower portion with surrounding edges seal around the perimeter of said tampon applicator.

18. The lubricated tampon system of claim 17, wherein said sanitary wrapper has a rear portion relative to said tampon having two free pull tabs so as to promote the quick breach of the sanitary wrapper for separation by peeling.

19. The lubricated tampon system of claim 17, wherein said sanitary wrapper comprises upper and lower inner adhesive strips so positioned as to adhere to said front end portion of said applicator cylinder, forming a lubrication pocket for containing lubrication therein.

* * * * *